United States Patent [19]
Toothman

[11] Patent Number: 6,001,572
[45] Date of Patent: Dec. 14, 1999

[54] METHOD OF IDENTIFYING ALOE USING PCR

[75] Inventor: Penelope Toothman, Boulder, Colo.

[73] Assignee: Univera Pharmaceuticals, Inc., Broomfield, Colo.

[21] Appl. No.: 08/899,786

[22] Filed: Jul. 24, 1997

Related U.S. Application Data

[60] Provisional application No. 60/022,611, Jul. 26, 1996.

[51] Int. Cl.$^6$ .............................. C12Q 1/68; C12P 19/34; C07H 21/04; C07H 21/02
[52] U.S. Cl. .......................... 435/6; 435/91.2; 536/24.33; 935/77; 935/78
[58] Field of Search ................... 435/6, 91.2; 536/24.33; 935/77, 78

[56] References Cited

FOREIGN PATENT DOCUMENTS 2 283 568   5/1995   United Kingdom .

OTHER PUBLICATIONS

Baker et al. (1996) S. Afr. J. Bot. 62:292–295.
Fangan et al. (1994) BioTechniques 16:484–493.
Taberlet et al. (1991) Plant Molecular Biology 17:1105–1109.
Cheung et al. (1994) Journal of Ethnopharmacology 42:67.
Kwan et al. (1992) Experimental Mycology 16:163.
Pang et al. (1992) Biosci. Biotech. Biochem. 56:1357.
Shaw and But (1995) Planta Med. 61:466.
Wang et al. (1993) Nucleic Acids Research 21:5930.
Welsh and McClelland (1990) Nucleic Acids Research 18:7213.
Welsh et al. (1991) Nucleic Acids Research 19:303.
Williams et al. (1990) Nucleic Acids Research 18:6531.

*Primary Examiner*—Stephanie W. Zitomer
*Attorney, Agent, or Firm*—Swanson & Bratschun LLC

[57] ABSTRACT

The present invention provides a method for the detection of species of Aloe using the polymerase chain reaction. The present invention also provides a method of differentiating between different species of Aloe using the polymerase chain reaction.

8 Claims, 3 Drawing Sheets

1. DNA standards
2. buffer control
3. Naturally Aloe drink
4. Naturally Aloe drink
5. Aloe-X-Gold
6. Aloe-X-Gold
7. Aloe vera 1:1 decolorized
8. Aloe vera 1:1 decolorized
9. DNA extraction control
10. DNA extraction control
11. dry leaf extract GnSCN 2A
12. dry leaf extract GnSCN 1A
13. A. barbadensis 0.5 fg
14. A. barbadensis 5 fg
15. A. barbadensis 50 fg

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE:

(xi) SEQUENCE DESCRIPTION: SEQ ID NO:1:

AATGTATTTG GTTTCAAAGC CC      22

(2) INFORMATION FOR SEQ ID NO:2:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE:

(xi) SEQUENCE DESCRIPTION: SEQ ID NO:2:

CTTTAATTTC ACCTGTTTCG GC      22

(2) INFORMATION FOR SEQ ID NO:3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE:

(xi) SEQUENCE DESCRIPTION: SEQ ID NO:3:

ATTTGAACTG GTGACACGAG      20

(2) INFORMATION FOR SEQ ID NO:4:

(i) SEQUENCE CHARACTERISTICS:
      (A) LENGTH: 20 base pairs
      (B) TYPE: nucleic acid
      (C) STRANDEDNESS: single
      (D) TOPOLOGY: linear

```
        (ii) MOLECULE TYPE:

(xi) SEQUENCE DESCRIPTION: SEQ ID NO:4:

GGTTCAAGTC CCTCTATCCC                                                     20

(2) INFORMATION FOR SEQ ID NO:5:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE:

(xi) SEQUENCE DESCRIPTION: SEQ ID NO:5:

TCTACCGATT TCGCCATATC                                                     20

(2) INFORMATION FOR SEQ ID NO:6:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE:

(xi) SEQUENCE DESCRIPTION: SEQ ID NO:6:

CATTACAAAT GCGATGCTCT                                                     20

(2) INFORMATION FOR SEQ ID NO:7:

(i) SEQUENCE CHARACTERISTICS:
             (A) LENGTH: 19 base pairs
             (B) TYPE: nucleic acid
             (C) STRANDEDNESS: single
             (D) TOPOLOGY: linear (ii) MOLECULE TYPE:

(xi) SEQUENCE DESCRIPTION: SEQ ID NO:7:

GGGATAGAGG GACTTGAAC                                                      19

(2) INFORMATION FOR SEQ ID NO:8:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE:

(xi) SEQUENCE DESCRIPTION: SEQ ID NO:8:

CGAAATCGGT AGACGCTACG                                                     20

(2) INFORMATION FOR SEQ ID NO:9:

(i) SEQUENCE CHARACTERISTICS:
             (A) LENGTH: 10 base pairs
             (B) TYPE: nucleic acid
             (C) STRANDEDNESS: single
             (D) TOPOLOGY: linear (ii) MOLECULE TYPE:

(xi) SEQUENCE DESCRIPTION: SEQ ID NO:9:
```

```
TGAGGGCCGT                                                                         10

(2) INFORMATION FOR SEQ ID NO:10:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:10:

CTGAAGCGCA                                                                         10

(2) INFORMATION FOR SEQ ID NO:11:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:11:

AAGACCGGGA                                                                         10

(2) INFORMATION FOR SEQ ID NO:12:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:12:

GACAGTCCCT                                                                         10

(2) INFORMATION FOR SEQ ID NO:13:

(i) SEQUENCE CHARACTERISTICS:
        (A) LENGTH: 1103 base pairs
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:13:

CGAAATCGGT AGACGCTACG GACTTGATTG GATTGAGCCT TAGTATGGAA                             50

ACCTGCTAAG TGGTAACTTC CAAATTCAGA GAATCCCTGG AACTAAAAAT                            100

GGGCAATCCT GAGCCAAATC TTTTTTTTTT TTTGAAAAAC TGATGAATCG                            150

GACAAGAATA AAAAAGATA GGTGCAGAGA CTCAATGGAA GCTGTTCTAA                             200

CGAATGGAGT TGATTACGTT GCGTTGGTAG CAGGAATCCT TCTTTCGAAA                            250

TTAAAGAAAG GATGACCTGT ATATCTAAGA CATACGTATA CATACTGACA                            300

TAGCAAACAA TTAATCACAA ACCGAATCCA TTACCATTAT ATATATATAT                            350

GCAAAATTCA GAGTTATTGT GGATCTATTC CAATCGACGT TGAAGGAAGA                            400

ATCGAATATT CAGTGATCCT ATCACTCATT CCAGAGTTTG ATAGGCCTTT                            450

TTTTTTTGAA AAACTGATGA ATTGGACGAG AATAAAGAGA GAGTCCCATT                            500
```

```
CTACATGTCA ATACCGACAA CAATGAAATT TATAGTAAGA GGAAAATCCG           550

TCGACTCTTA GAAATCGTGA GGTCAAGTCC CTCTATCCCC AATAAAAAGC           600

CCATTTTTCC CCATAAAAAG CCCATTTTAC TTCTTAACTA TACTATTTAT           650

CTTCTTTTTT TTTCATAAGT AGTTCAAGTT CAAAGAAAAT TCAATATCTT           700

TCTCATTGAT TCTACCCTTT CCCAAACAAA TGGGTCCGAA TAGATTTTTG           750

TCTTATCCCA ATTTGGTTTG AATAGATACG ATATCTGTGC ATATGAATAT           800

ATATGGGCAA GGAATTTCCA TTGTTGAATC ATTCACAGCC CATATCAGTA           850

TTTTTCCATT TACAAATACA AAGAAAGTCT TCTTTTTGAA GATCTAAGAA           900

ATTCATGGAC TAGGTCAATT TTTTGAATAC TTTAATTTAA ATATTTCAAT           950

GATTTTTTTT TTTTAATAAT TAATATTGAA TTTCTTTATT TTTTAGTCTA          1000

TTTAATTTAC CAAGCACTCT ACTAGGATGA TGCGCGGGAA ATGGTCGGGA          1050

TAGCTCAGTT GGTAGAGCAG AGGACTGAAA ATCCTCGTGT CACCAGTTCA          1100

AAT                                                            1103

(2) INFORMATION FOR SEQ ID NO:14:

(i) SEQUENCE CHARACTERISTICS:
        (A) LENGTH: 520 base pairs
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:14:

CTTGATTGGA TTGAGCCTTA GTATGGAAAC CTGCTAAGTG GTAACTTCCA            50

AATTCAGAGA ATCCCTGGAA CTAAAAATGG GCAATCCTGA GCCAAATCTT           100

TTTTTTTTTT TGAAAAACTG ATGAATCGGA CAAGAATAAA AAAGATAGG            150

TGCAGAGACT CAATGGAAGC TGTTCTAACG AATGGAGTTG ATTACGTTGC           200

GTTGGTAGCA GGAATCCTTC TTTCGAAATT AAAGAAAGGA TGACCTGTAT           250

ATCTAAGACA TACGTATACA TACTGACATA GCAAACAATT AATCACAAAC           300

CGAATCCATT ACCATTATAT ATATATATGC AAAATTCAGA GTTATTGTGG           350

ATCTATTCCA ATCGACGTTG AAGGAAGAAT CGAATATTCA GTGATCCTAT           400

CACTCATTCC AGAGTTTGAT AGGCCTTTTT TTTTTGAAAA ACTGATGAAT           450

TGGACGAGAA TAAAGAGAGA GTCCCATTCT ACATGTCAAT ACCGACAACA           500

ATGAAATTTA TAGTAAGAGG                                            520

(2) INFORMATION FOR SEQ ID NO:15:

(i) SEQUENCE CHARACTERISTICS:
        (A) LENGTH: 574 base pairs
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:15:

GTAGACGCTA CGGACTTGAT TGGATTGAGC CTTAGTATGG AAACCTGCTA            50

AGTGGTAACT TCCAAATTCA GAGAATCCCT GGAACTAAAA ATGGGCAATC           100

CTGAGCCAAA TCTTTTTTTT TTTTTGAAAA ACTGATTAAT CGGACAAGAA           150
```

```
TAAAAAAAAA TGGGTGCAGA AACTCAATGG AAGCTGTTCT AACGAATGGA          200

GTTGATTACG TTGCCTTGGT AGCAGGAATC CTTCTTTCGA AATTAAAGAA          250

AGGATGACCT ATATATCTAA GACATACGTA TACATACTGA CATAGCAAAC          300

AATTAATCAC AAACCGAATA CATTATATAT TATATATTAT AATGTATATG          350

CAAAATTCAG ATTTATTGTG GATCTATTCC ATTCGACGTT GAAGGAAGAA          400

TCGAATATTC AGTGATCCTA TCACTCATTC CAGAGTTTGA TAGGCCCTTT          450

TTTTTTTTTG AAAAACTGAT AAATTGGACG AGAATAAAGA GAGAGTCCCA          500

TTCTACATGT CAATACCGAC AACAATGAAA TTTATAGTAA GAGGAAAATC          550

CGTCGACTCT TAGAAATCGT GAGG                                      574

(2) INFORMATION FOR SEQ ID NO:16:

(i) SEQUENCE CHARACTERISTICS:
        (A) LENGTH: 562 base pairs
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:16:

GACTTGATTG GATTGAGCCT TAGTATGGAA ACCTGCTAAG TGGTAACTTC           50

CAAATTCAGA GAATCCCTGG AACTAAAAAT GGGCAATCCT GAGCCAAATC          100

TTTTTTTTTT TGAAAAACTG ATTAATCGGA CAAGAATAAA AAAAGATAGG          150

TGCAGAGACT CAATGGAAGT TGTTCTAACG AATGGATTTG ATTACGTTGC          200

GTTGGTAGCA GGAATCCTTC TTTCGAAATT AAAGAAAGGA TGACCTATAT          250

ATCTAAGACA TACGTATACA TACTGACATA GCAAACAATT AATCACGAAC          300

CGAATACATT ATATATGATA TATTATTTAT GTATATGCAA AATTCAGAGT          350

TATTGTGGAT CTATTCCAAT CGACGTTGAA GGAAGAATCG AATATTCAGT          400

GATCCTATCA CTCATTCCAG AGTTTGATAG GCCCTTTTTT TTTTTTTGAA          450

AAACTGATAA ATTGGACGAG AATAAAGAGA GAGTCCCATT CTACATGTCA          500

ATACCGACAA CAATGAAATT TATAGTAAGA GGAAAATCCG TCGACTCTTA          550

GAAATCGTGA GG                                                   562

(2) INFORMATION FOR SEQ ID NO:17:

(i) SEQUENCE CHARACTERISTICS:
        (A) LENGTH: 479 base pairs
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:17:

TCCCCAATAA AAAGCCCATT TTACTTCTTA ACTATACTAT TTATCTTCTT           50

TTTTTTTCAT AAGTAGTTCA AGTTCAAAGA AAATTCAATA TCTTTCTCAT         100

TGATTCTACC CTTTCCCAAA CAAATGGGTC CGAATAGATT TTTGTCTTAT         150

CCCAATTTGG TTTGAATAGA TACGATATCT GTGCATATGA ATATATATGG         200

GCAAGGAATT TCCATTGTTG AATCATTCAC AGCCCATATC AGTATTTTTC         250

CATTTACAAA TACAAAGAAA GTCTTCTTTT TGAAGATCTA AGAAATTCAT         300
```

```
GGACTAGGTC AATTTTTTGA ATACTTTAAT TTAAATATTT CAATGATTTT                   350

TTTTTTTTAA TAATTAATAT TGAATTTCTT TATTTTTTAG TCTATTTAAT                   400

TTACCAAGCA CTCTACTAGG ATGATGCGCG GGAAATGGTC GGGATAGCTC                   450

AGTTGGTAGA GCAGAGGACT GAAAATCCT                                          479
```

(2) INFORMATION FOR SEQ ID NO:18:

(i) SEQUENCE CHARACTERISTICS:
        (A) LENGTH: 484 base pairs
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:18:

```
TCCCTCTATC CCCAATAAAA AGCCCATTTT ACTTCTTAAC TATACTATTT                    50

ATCTTCTTTT TTTTTTCATA AGTAGTTCAA AGAAAAATTC AATATCTTTC                   100

TCATTGATTC TACCCTTTCC CAAACAAATG GGTCCGAATA AATTTTTGTC                   150

TTATCCCAAT TTGGTTTGAA TAAATACAAT ATCCGTGCAT ATGAATATAT                   200

ATGGGCAAAA AATTTCCATT GTTGAATCAT TCACAGCCCA TATCAGTATT                   250

TTTCCATTTA CAAATACAAA GAAAGTCTTC TTTTTGAAGA TCTAAAAAAT                   300

TCATGGACTA GGTCAATTTT TTGAATACTT TAATTTCAAT ATTTAAATGA                   350

TTTTTTTTTA AATATATGAA TTTCTTTATT TTTTAGTCTA TTTAATTTAC                   400

CAAGCACTCT ACTAGGATGA TGCGCGGGAA ATGGTCGGGA TAGCTCAGTT                   450

GGTAGAGCAG AGGACTGAAA ATCCTCGTGT CACC                                    484
```

(2) INFORMATION FOR SEQ ID NO:19:

(i) SEQUENCE CHARACTERISTICS:
        (A) LENGTH: 494 base pairs
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:19:

```
TCAAGTCCCT CTATCCCCAA TAAAAAGCCC ATTTTACTTC TTAACTATAC                    50

TATTTATCTT CTTTTTTTTT TCATAAGTAG TTCAAAGAAA AATTCAATAT                   100

CTTTCTCATT GATTCTACCC TTTCCCAAAC AAATGGGTCC GAATAGATTT                   150

TGTCTTATC CCAATTTGGT TGAATAAAT ACAATATCTG TGCATATGAA                     200

TATATATGGG CAAAGAATTT CCATTGATAA ATCATTCACA GCCCATATCA                   250

GTATTTTTCC ATTTACAAAT ACAAAGAAAG TCTTCTTTTT GAAGATCTAA                   300

AAAATTTATG GACTAGGTCA ATTTTTTGAA TACTTTAATT TCAATATTTA                   350

AATGATTTTT TTTATATTA ATATGAATTT CTTTATTTTT TAGTCTATTT                    400

AATTTACCAA GCACTCTACT AGGATGATGC GCGGGAAATG GTCGGGATAG                   450

CTCAGTTGGT AGAGCAGAGG ACTGAAAATC CTCGTGTCAC CAGT                         494
```

(2) INFORMATION FOR SEQ ID NO:20:

(i) SEQUENCE CHARACTERISTICS:
        (A) LENGTH: 246 base pairs
        (B) TYPE: nucleic acid (C) STRANDEDNESS: single
        (D) TOPOLOGY: linear (ii) MOLECULE TYPE:

(xi) SEQUENCE DESCRIPTION: SEQ ID NO:20:

CACTCCAAGG ANAAATGGTC TTCTCTCTAT GAGATACACT CACAACAGAA          50

AGAGAAGTCA TCACTGCACT GACAAAACAT AATGGCTCCA CCTGAAAGTT         100

TGTATGGTGA AAAGAGCCCA AAAGAACACC TCAATGGATG TNGCCAACCT         150

GGATATGAAT AAAGCTCTGG AAAGAAGGAA ACTCTGTGGT GTTTTCCAAT         200

GAACCACTCA TACCACAAAT CCACAATCGA TCACCAACCA TATCTG             246

(2) INFORMATION FOR SEQ ID NO:21:

(i) SEQUENCE CHARACTERISTICS:
        (A) LENGTH: 117  base pairs
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:21:

CTGAGTACTG TCAGATATCA TGCTTGTCTG CATATTGTAT GAAGGCATAA          50

ACATCCATGA GCTACGCTAC CTTAGAATCC GAGTACTACC GCGCCATGAT        100

ATAGTCTTCA CCGTCAC                                             117

(2) INFORMATION FOR SEQ ID NO:22:

(i) SEQUENCE CHARACTERISTICS:
        (A) LENGTH: 458  base pairs
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:22:

CCTTGTGGTG TGGACTACAT GTCAGGATTC AGGTGTACTC CGGCATCTGG          50

TCTACTAACT CGCTTAGACC CCTTACCTTT CTCACAGATG AATAGTTGAA         100

CCTCTANNCT AATTTTATAA GATGTAGCTC CATTTGTGAA TTTCTAGACC         150

GGATCATAAT TTATGTACGG GTATCAAGTA TCTTAATGCT TTGTAGACAT         200

GCTCTCACCC ATACGGAAAG GTCCCTGACT GGTCGGAAAT TCGCGCTCCA         250

TCACCCCGAC CCCATGTATA GGTTAGTATT TCCTTCCGGA TGCTTGTTAC         300

AGCTCCGCGA GGTGACCGNA CGTCTTAGTA TATTCCCTTG TGTTATATTT         350

CCCCTTGAGT AATATAAGAG ACTGATCAAT TGACGGCATA ATTATCATAC         400

TTGTAAAATT CTAATATCTG CATGTCTCAT GCCTAATTAG AATATGATGA         450

TAAGTCCA                                                       458

(2) INFORMATION FOR SEQ ID NO:23:

(i) SEQUENCE CHARACTERISTICS:
        (A) LENGTH: 213 base pairs
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:23:

TCTGGAGTAC CTATGGACCA GTACCGAGAA ATGATTTCCT GAAACAGATT          50

TTGGAAAAGA ACAATTATAA TTTAGCCGGG GAAGATTTTA CTCATATATT         100

CCGAAAGAAT TAGCCATATC TAATATTAAT GATGATCATG CATGTTCTCA         150

GAGAGTCATG TATATGGAGC CCGGGACCAC CTCAATCGAG ATACCAGTAG         200

GTCCCAGAAC AAA                                                  213

(2) INFORMATION FOR SEQ ID NO:24:

(i) SEQUENCE CHARACTERISTICS:
            (A) LENGTH: 406 base pairs
            (B) TYPE: nucleic acid
            (C) STRANDEDNESS: single
            (D) TOPOLOGY: linear (ii) MOLECULE TYPE:

(xi) SEQUENCE DESCRIPTION: SEQ ID NO:24:

GAGAGATCCA GTCGATCACT ATAAATGTGG ATCTTAGCCC AACTGTTCGG          50

CATACTGGAG ATCCTCCATC GGTAGGATAC GGATCCCCTG TCTCAAAATC         100

ATCCTCATAC AAACCTCATG CACCATGGTC CTGGTGGTCA ACTAAGCTGT         150

CAGATAAAGT AGCCAAATAA CAGAATACAT CTAGATAATA ACTGCAGAGA         200

AATACTGATA TGAACTAACA GGTATGCAAT GGAAAATACT ACAGTTGTTA         250

TCTTTCGTCC ATTTTATTAA TGGTTGGAGA GCATAATCTA ACAATAATGG         300

CTCAACGGAT ACCCACAGGG TGGATATCTG TATCACAGGT ACCGATATCT         350

AGCTCAATGC ATTGTCATCA ACCTTCACAT CGGCATGCCG TATCCCTTTC         400

CCAAAC                                                          406

(2) INFORMATION FOR SEQ ID NO:25:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE:

(xi) SEQUENCE DESCRIPTION: SEQ ID NO:25:

CAAACCGAAT CCATTACC                                             18

(2) INFORMATION FOR SEQ ID NO:26:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE:

(xi) SEQUENCE DESCRIPTION: SEQ ID NO:26:

TTGAATTTTC TTTGAACTTG                                           20

(2) INFORMATION FOR SEQ ID NO:27:

(i) SEQUENCE CHARACTERISTICS:
            (A) LENGTH: 21 base pairs
            (B) TYPE: nucleic acid
            (C) STRANDEDNESS: single (D) TOPOLOGY: linear (ii) MOLECULE TYPE:

(xi) SEQUENCE DESCRIPTION: SEQ ID NO:27:

GATAGGTGCA GAGACTCAAT G                                                      21

(2) INFORMATION FOR SEQ ID NO:28:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:28:

AGACAAAAAT CTATTCGGA                                                         19

(2) INFORMATION FOR SEQ ID NO:29:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:29:

CTGCACTGAC AAAACATAAT G                                                      21

(2) INFORMATION FOR SEQ ID NO:30:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:30:

GATCGATTGT GGATTTGTG                                                         19

(2) INFORMATION FOR SEQ ID NO:31:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:31:

CCTGTCTCAA AAATCATCCT C                                                      21

(2) INFORMATION FOR SEQ ID NO:32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:32:

TGTGAAGGTT GATGACAATG                    20

METHOD OF IDENTIFYING ALOE USING PCR

This application claims benefit of provisional application 60/022,611 filed on Jul. 26, 1996.

FIELD OF INVENTION

The present invention relates generally to a method of identifying Aloe using the polymerase chain reaction. Also included in the present invention is a method of differentiating between different species of Aloe using the polymerase chain reaction. The method of the present invention can be extended to the determination of the amount of Aloe present in a mixture.

BACKGROUND OF THE INVENTION

Aloe is a simple plant with an elaborate set of biologically active substances. (Cohen et al. in *Wound Healing/Biochemical and Clinical Aspects*, 1st ed. W. B. Saunders, Philadelphia (1992)). Over 300 species of Aloe are known, most of which are indigenous to Africa. Studies have shown that the biologically active substances are located in three separate sections of the aloe leaf—a clear gel filet located in the center of the leaf, in the leaf rind or cortex of the leaf and in a yellow fluid contained in the pericyclic cells of the vascular bundles, located between the leaf rind and the internal gel filet, referred to as the latex. Historically, Aloe products have been used in dermatological applications for the treatment of burns, sores and other wounds. These uses have stimulated a great deal of research in identifying compounds from Aloe plants that have clinical activity, especially anti-inflammatory activity. (See, e.g., Grindlay and Reynolds (1986) J. of Ethnopharmacology 16:117–151; Hart et al. (1988) J. of Ethnopharmacology 23:61–71). As a result of these studies there have been numerous reports of Aloe compounds having diverse biological activities, including anti-tumor activity, anti-acid activity (Hirata and Suga (1977) Z. Naturforsch 32c:731–734), anti-diabetic activity, tyrosinase inhibiting activity (Yagi et al. (1987) Planta medica 515–517), and antioxidant activity (International Application Serial No. PCT/US95/07404, published Dec. 19, 1996, publication number WO 96/40182). Aloe products are also used extensively in the cosmetic industry to protect skin against ultraviolet light. (Strickland et al. (1994) J. Invest. Dermatol. 102:197; Grollier et al. U.S. Pat. No. 4,656,029, issued Apr. 7, 1987).

The commercial use of Aloe is wide spread, particularly in the cosmetic industry. There are currently many commercially available products which contain Aloe as an ingredient, however, to date there is there is no commercially viable process for the detection or quantitation of the amount of Aloe in these products. In order to better regulate this industry, there is currently a need for a process to detect and quantitate the amount of Aloe present in a mixture. At present manufacturers and distributors of Aloe can adulterate and dilute Aloe products and go undetected. It is imperative to develop standards to protect the Aloe product name.

The Polymerase Chain Reaction (PCR), is a recently developed technique which has had a significant impact in many areas of science. PCR is a rapid and simple method for specifically amplifying a target DNA sequence in an exponential manner. (Saiki et al. (1985) Science 230:1350; Mullis and Faloona (1987) Methods Enzymol. 155:335). Briefly, the method consists of synthesizing a set of primers that have nucleotide sequences complementary to the DNA that flanks the target sequence. The primers are then mixed with a solution of the target DNA, a thermostable DNA polymerase and all four deoxynucleotides (A, T, C and G). The solution is then heated to a temperature sufficient to separate the complementary strands of DNA (approximately 95° C.) and then cooled to a temperature sufficient to allow the primers to bind efficiently and specifically to the flanking sequences. The reaction mixture is then heated again (to approximately 72° C.) to allow the DNA synthesis to proceed. After a short period of time the temperature of the reaction mixture is once again raised to a temperature sufficient to separate the newly formed double-stranded DNA, thus completing the first cycle of PCR. The reaction mixture is then cooled and the cycle is repeated. Thus, PCR consists of repetitive cycles of DNA melting, annealing and synthesis. Twenty replication cycles can yield a million fold amplification of the target DNA sequence. The ability to amplify a single DNA molecule by PCR has applications in environmental and food microbiology (Wernars et al. (1991) Appl. Env. Microbiol. 57:1914–1919; Hill and Keasler (1991) Int. J. Food Microbiol. 12:67–75), clinical microbiology (Wages et al. (1991) J. Med. Virol. 33:58–63; Sacramento et al. (1991) Mol. Cell Probes 5:229–240; Laure et al. (1988) Lancet 2:538), oncology (Kumar and Barbacid (1988) Oncogene 3:647–651; McCormick (1989) Cancer Cells 1:56–61; Crescenzi et al. (1988) Proc. Natl. Acad. Sci. USA 85:4869), genetic disease prognosis (Handyside et al. (1990) Nature 344:768–770), blood banking (Jackson (1990) Transfusion 30:51–57) and forensics (Higuchi et al. (1988) Nature (London) 332:543). PCR has also been used in phylogenetic studies of various organisms. For example, PCR has been used to authenticate and differentiate three medical species of Panax from one another and also from their common adulterants. (Shaw and But (1995) Planta Med. 61:466–469; Cheung et al. (1994) J. Ethnopharmacol. 42:67–69).

The feasibility of using the polymerase chain reaction to identify Aloe depends on establishing specific primers that detect Aloe DNA and extraction protocols that reproducibly recover the DNA. The proportion of Aloe DNA which survives processing and the successful recovery of DNA and elimination of PCR inhibitory substances from DNA extracts will dictate the sensitivity of the PCR reaction necessary to detect Aloe DNA in extracts of industrial Aloe products. The sensitivity of the PCR reaction that is required defines the type of PCR-product detection-system that is necessary and the type of containment required to eliminate spurious results and possible contamination.

SUMMARY OF THE INVENTION

The present invention includes a method of identifying Aloe using the polymerase chain reaction. Specifically, the present invention includes a method for detecting the presence Aloe in an industrial product. In one embodiment of the present invention, the method comprises extracting DNA from a sample, amplifying the DNA using PCR, and comparing the PCR products obtained with PCR products obtained from a known sample of Aloe. In a preferred embodiment the species of Aloe is selected from *Aloe barbadensis, Aloe capensis* or *Aloe arborescins*. In the most preferred embodiment the species of Aloe is *Aloe barbadensis*. In one embodiment of the present invention universal PCR primers are used. In a second embodiment novel primers specific for a particular species of Aloe are identified and used in the PCR reaction. The present invention includes the PCR primers so identified. The use of novel primers results in greater specificity and assurance that any PCR products obtained from test reactions is indicative of the presence of Aloe DNA and not another plant species or just a band of spurious nature. Use of novel primers in a nested fashion further validates the assay.

The present invention also includes a method for differentiating between different species of Aloe using the polymerase chain reaction. The method for differentiating between different species of Aloe comprises extracting DNA from an unknown sample, amplifying the DNA using the PCR reaction and comparing the PCR products obtained from the unknown sample with PCR products obtained from known species of Aloe. In this embodiment of the present invention the PCR primers can be universal primers or novel primers specific for a particular species of Aloe.

The method of the present invention can be extended to the quantitation of the amount of Aloe present in a particular sample.

It is to be understood that both the foregoing general description and the following detailed description are exemplary and explanatory only and are not restrictive of the invention as claimed.

DETAILED DESCRIPTION OF THE INVENTION

Figure 1:
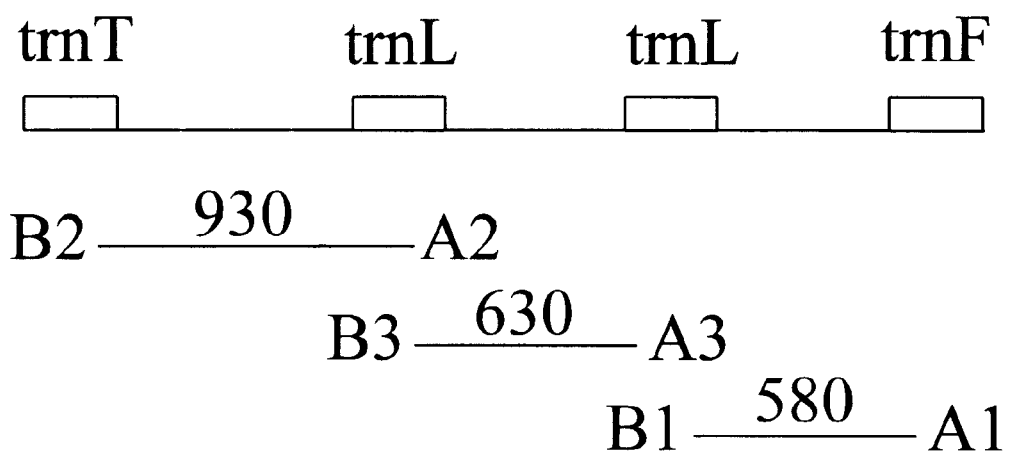
FIG. 1 depicts the chloroplast tRNA genes trnT, trnL, and trnF, together with the length of the PCR fragments obtained using the indicated primers. The trnL gene is split because it contains an intron.

The present invention includes a method of detecting Aloe DNA. Specifically, the present invention includes a method for detecting the presence Aloe in an industrial product using the polymerase chain reaction. In one embodiment of the present invention, the method comprises extracting DNA from a sample, amplifying the DNA using PCR, and comparing the PCR products obtained with PCR products obtained from a known sample of Aloe. In a preferred embodiment the species of Aloe is selected from *Aloe barbadensis, Aloe capensis* or *Aloe arborescins*. In the most preferred embodiment the species of Aloe is *Aloe barbadensis*. In one embodiment of the present invention commercially available universal PCR primers are used in the polymerase chain reaction. In a second embodiment novel primers specific for a particular species of Aloe are identified and used in the PCR reaction. The use of novel primers results in greater specificity. The present invention includes the PCR primers so identified.

The present invention also includes a method for differentiating between different species of Aloe using the polymerase chain reaction. The method for differentiating between different species of Aloe comprises extracting DNA from an unknown sample containing Aloe, amplifying the DNA using the PCR reaction and comparing the PCR products obtained from the unknown sample with PCR products obtained from known species of Aloe. In this embodiment of the present invention the PCR primers can be universal primers or novel primers specific for a particular species Aloe.

The method of the present invention can be extended to the quantitation of the amount of Aloe present in a particular sample.

Certain terms used to describe the invention herein are defined as follows:

The term "Aloe" refers to the genus of plants found worldwide from the Liliaceae family of which the *Aloe barbadensis* (*A. barbadensis*), *Aloe capensis* (*A. capensis*), and *Aloe arborescins* (*A. arborescins*) plants are species.

The term "dry leaf extracts" is defined as the dried juice of the whole leaf of various species of the Aloe plant. The "whole plant" *Aloe vera* used in the examples of this invention was prepared by "whole-leaf processing" of the whole leaf of the *Aloe barbadensis, Aloe capensis* and *Aloe arborescins* plants. Briefly, whole leaves obtained from the specific Aloe plant were ground, filtered, treated with cellulase (optional), activated carbon, diatomaceous earth, and lyophilized. The lyophilized powder was reconstituted in aqueous solution prior to use.

As used herein a "primer" is a nucleotide sequence used in PCR to amplify a segment of DNA. The primers identified by the method of this invention are nucleotide sequences of at least 10 bases that can be used to prime DNA synthesis and amplify a segment of Aloe DNA or a segment of one or more of a particular species of Aloe DNA. The primers identified by the method of this invention can also be used as hybridization probes.

A "fragment" of a nucleotide sequence is some portion of the whole DNA sequence that can perform the same function as the whole sequence, either as a PCR primer, a PCR template or hybridization probe. In a preferred embodiment a "fragment" will have at least 12 contiguous bases.

As stated above, the feasibility of using the polymerase chain reaction to identify Aloe depends on establishing specific primers that detect Aloe DNA and extraction protocols that reproducibly recover the DNA. Example 1 describes a number of different methods of extracting DNA from Aloe and solutions containing extract from Aloe. The DNA extractions using GnSCN/isopropanol (Example 1) give the most reproducible banding patterns with the greatest number of primers (A1B3, A3B3, OPAE-10, rbcL and OPAE-19, discussed below).

To develop an assay for the detection of Aloe using the polymerase chain reaction, PCR primers must be defined which are specific for Aloe and amplify segments of Aloe DNA in a reproducible manner with the minimum number of spurious artifacts, resulting from the amplification of non-target oligonucleotides due to side-reactions, such as mispriming of background DNA and/or primer oligomerization, and give yields as close as possible to theoretical yields in order to result in an assay of adequate sensitivity. The only DNA sequence information which was available for Aloe was a portion of the rbcL gene, one of the most conserved proteins in phylogeny, ribulose 1,5-bisphosphate. This sequence was not a good candidate for developing specific primers since it is so highly conserved. Two different approaches to developing specific primers were taken using commercially available DNA primers, as described below. All PCR reactions were performed as described in Example 2.

tRNA Genes

The universal chloroplast tRNA primers (Table 1, SEQ ID NOS:1–12) take advantage of the extreme conservation of the tRNA genes (Taberlet et al. (1991) Plant Molecular Biology 17:1105–1109). The advantage of these markers is that the length of the PCR fragments is characteristic of the species. This is because these primers amplify contiguous non-coding regions which display higher frequencies of mutations than the gene sequences. Such non-coding regions can potentially be exploited for validation of species identification because of the unique DNA sequence information obtained. The PCR reactions were performed using the chloroplast tRNA primers set forth in Table 1 (SEQ ID NOS:1–12). Referring to FIG. 1, primer pair A2:B2 amplifies a 930 base pair (bp) intergenic fragment between genes trnT and trnL. Primer pair A3:B3 amplifies a 630 bp fragment containing the intron in the trnL gene and primer pair A1:B1 amplifies a 580 bp fragment containing the intergenic region between genes trnL and trnF. These three fragments are 773, 577 and 438 bp in tobacco; 833, 614 and 324 bp in rice, and 251, 389, and 158 bp in marchantia.

No obvious length polymorphisms were detected among *Aloe barbadensis*, *Aloe capensis* and *Aloe arborescins* species of Aloe for the A1B1 and A3B3 bands under the electrophoresis conditions used. DNA sequencing of the A1B3 region from all three species, however, indicated small insertions and deletions of DNA which have been exploited to make *Aloe barbadensis* specific PCR primers. It is possible that these same deletions could be also exploited to make *Aloe capensis* or *Aloe arborescins* specific primers.

The published sensitivity of the assay with universal cpDNA primers was 10 ng total DNA per reaction. (Taberlet et al. (1991) Plant Molecular Biology 17:1105–1109). Using the conditions set forth in Example 2, detection of 50 fg of the A3B3 and A1B3 fragments, 500 fg of A1:B1 and 5 pg of A2B2 was routinely achieved. These sensitivities were achieved with 45 cycles of 94° C.-$T_A$-72° C. with 1 minute segments where the annealing temperature ($T_A$ was 54.3° C. for A1B3 and A3B3, 52° C. for A1B1 and 50° C. for A2B2.

Semi-Nested PCR

Figure 2:
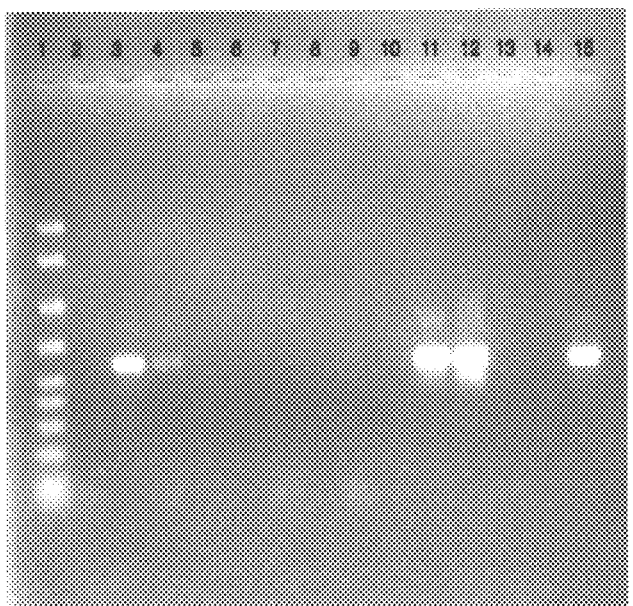
FIG. 2 shows semi-nested PCR results for GnSCN/isopropanol extractions of dry leaf extract (Example 1), NaCl/isopropanol precipitations of Aloe gel (Example 1), Aloe X Gold and Naturally ALOE drink (Example 1).
Figure 3:
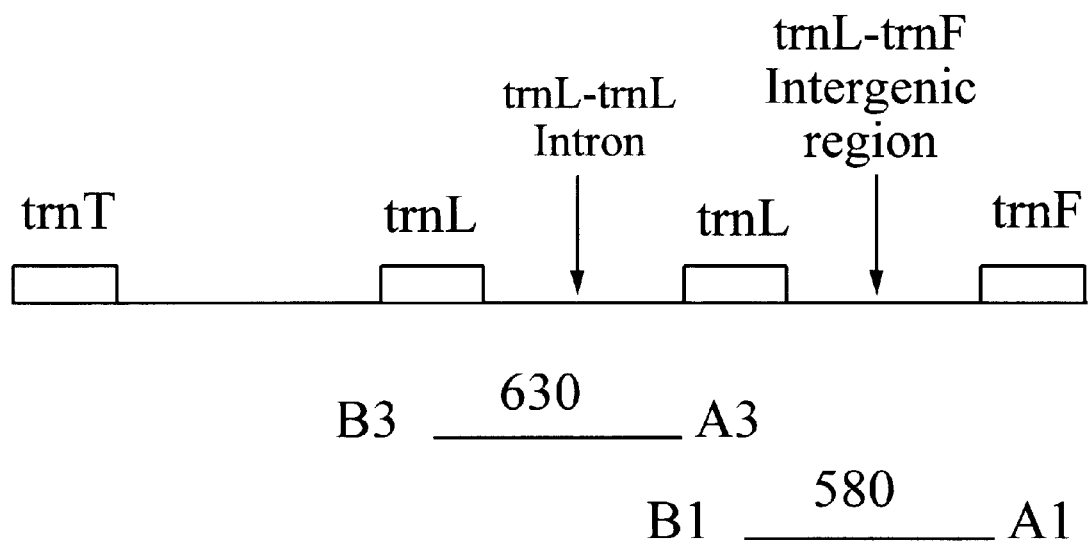
FIG. 3 illustrates the location of the intron of tRNA L and the intergenic region between tRNA L and tRNA F.

Semi-nested PCR using the A1B3 primers for 31 cycles (94° C.-54.3° C.-72° C.; 1 minute-2 minutes-1 minute) followed by A3B3 for 21 cycles (using the same conditions) gave a strong signal at 50 fg total DNA. The signal strength is much greater and the specificity is increased by semi-nesting the primers. For example, 50 fg as opposed to 5 ng of DNA can be detected in 21 cycles due to preamplification with the A1B3 primer set. FIG. 2 shows semi-nested PCR results for GnSCN/isopropanol extractions of dry leaf extract (Example 1), NaCl/isopropanol precipitations of Aloe gel (Example 1), Aloe X Gold and Naturally ALOE drink.

DNA concentrations are estimated by limiting dilution. Actual quantitation of relative amounts of DNA requires an internal PCR control in each sample. The estimated DNA concentrations are shown in Table 2.

The DNA content of the dry leaf extract has been adjusted to a wet weight basis, assuming the freeze dry gel is a 200 fold concentrate. Dry leaf extract has only $1.8 \times 10^{-9}$ the amount of DNA as fresh tissue. This is not particularly surprising, since the magnesium rich tissue is ground and nucleases are released with ample opportunity to degrade the DNA. Additionally, charcoal is a very efficient adsorbent of nucleic acids and diatomaceous earth may also remove DNA.

To increase specificity, the A1B1 and A3B3 fragments were sequenced using standard methods and appropriate universal chloroplast DNA (cp DNA) primers in order to identify novel primers that are in the intron of trnL and the intergenic region between trnL and trnF. There is function associated with the intron in the trnL gene, but homology to other sequenced chip genomes should show which regions are essential and conserved. Clearly the whole sequence is not essential since the length varies from species to species. The intergenic region has no known function so presumably its sequence will be drifting independently in all species of green plants. There is very little repetitive DNA in chloroplasts. PCR primers from the intron/intergenic region will be universal if selected from conserved regions, but specific to Aloe if they span non-conserved regions and depending on the mutation rate and precise placement of substitutions may even be chosen to be specific for different species of Aloe, particularly *Aloe barbadensis*. After sequencing the above fragments new primers were chosen from the Aloe trnL intron and the trnL-F intergenic region according to the rules known to give good primers (see Tables 3–5). All primers tested to make Aloe and *Aloe barbadensis* specific assays are underlined.

RAPD Primers

RAPD primers are short (10 bp) and thus are not unique with respect to large genome sequences. Screening with RAPD primers virtually guarantees that PCR bands will be obtained with any source of DNA, because of the frequent representation of a random fragment only 10 bp long. The patterns may also be complex when RAPD primers amplify repetitive DNA. Towards limiting dilutions of DNA the size and integrity of DNA can grossly effect the PCR banding pattern with RAPD primers. The difficulty involved in using RAPD primers involves sorting through the patterns to find band patterns that are reproducible over a wide range of DNA concentrations and are not grossly effected by DNA integrity. Out of 20 RAPD primers initially screened (OPAE-1–20 from Operon Technologies), four (OPAE-1, OPAE-10, OPAE-11 and OPAE-19) were determined to have adequate sensitivity. PCR studies indicate that OPAE-11 and OPAE-19 may be useful for distinguishing among the Aloe species, but only OPAE-19 would be useful to identify Aloe DNA in industrial extracts (data not shown).

OPAE-19 PCR

Primer OPAE-19 gave a reproducible PCR band pattern for all of the GnSCN/isopropanol precipitated dry leaf extract samples (data not shown). The same pattern of DNA bands is observed with 5–20 pg DNA unsheared total DNA from fresh tissue. With 5 pg total of *Aloe barbadensis* DNA, OPAE-19 gives primarily a quartet of bands approximately 450, 700, 800 and 1000 bp long, which were sequenced using standard methods. Briefly, the OPAE-19 PCR fragments from *Aloe barbadensis* were separated by gel electrophoresis, eluted from the gel, screened with restriction enzymes for those making a single cut, and finally the two ends of each restricted PCR fragment were purified by gel electrophoresis and sequenced (Tables 6–8).

Using standard DNA extracted from plants according to methods in Example 1, the sensitivity of the OPAE-19 and the chloroplast primers A1B3 or A3B3 were all 0.05 pg in a limiting dilution assay. The OPAE-19 assay of the GnSCN industrial extract indicated that much more DNA was present (approximately 5–10 pg as opposed to the 0.05 pg from limiting dilution of total DNA from the chloroplast assay). This may simply reflect the fact that these amplified segments are in very long DNA in the standard and very short DNA in the industrial product or that chloroplast DNA is preferentially degraded by industrial processing. Thus DNA extracted directly from leaves versus DNA extracted from industrial products may differ quantitatively in the ratio of markers. The ratio of markers would then be characteristic of the source of the DNA.

Aloe Specific PCR Assays

Four sets of primers have been identified which are useful for identifying Aloe DNA (Table 9). Three of the four sets of primers identified (OPAE19-4f/OPAE19-4r, OPAE19-8f/

OPAE19-8r and aloe-f/aloe-r) amplify DNA from all three species of Aloe tested. The OPAE19-8 primers amplify the correct size DNA fragment, but only at very high template concentrations. The OPAE19-4 and aloe-r and f primer sets can amplify small quantities of Aloe DNA standards and offer two independent markers to confirm the presence of Aloe DNA in a sample. Search of the NCBI data base with BLASTN shows that the OPAE19-4 sequence is unique to Aloe and is not chloroplast DNA. Data base analysis shows that primer pair aloe-f and aloe-r are specific for chloroplast DNA of the Aloe species and could not prime any other plant chloroplast genome in the trnL-F region.

A. barbadensis Specific PCR Assay

All possible chloroplast primer pairs (Table 9) amplify A. barbadensis chloroplast DNA. Primers av-f and av-r amplify A. barbadensis DNA, but fail to amplify A. arborescins and A. capensis. The observed specificity for amplification of A. barbadensis is in agreement with sequence data in Tables 4 and 5 and the known theoretical requirements for efficient priming. A data base search of the NCBI data base with BLASTN shows that these primers have no fortuitous match with any other chloroplast genome in the trnL-F region that has been sequenced. Where stringent identification of A. barbadensis DNA in industrial extracts is desired a nested or semi-nested PCR reaction can be used. All appropriate primer pairs of chloroplast primers (Table 9) can be used in a nested or semi-nested fashion. The routine sensitivity of the semi-nested assays is 0.05 pg total DNA per tube.

To determine the amount of Aloe in a unknown sample, the sample is spiked with an internal control, such as radioactively labeled DNA from a species other than Aloe, and the DNA is then extracted from the sample using standard means. The radioactive exogenous DNA serves as an internal control to estimate the recovery of DNA by the extraction procedure and validate the extraction process. In cases where the internal control is not adequately recovered the extraction procedure is adjusted until recovery is adequate and reproducible. This can be accomplished, for example, by increasing the carrier nucleic acid or the alcohol concentrations in the precipitations.

The Aloe DNA extracted from the unknown sample is then simultaneously amplified with non-homologous DNA by PCR using primers specific for the Aloe species of interest and primers specific for the non-homologous DNA. The non-homologous DNA is added to the samples prior to PCR to serve as an internal control template. The PCR control template can be any target of similar, but not identical size that does not interfere with the amplification of Aloe DNA. The purpose of the internal control is to ensure that there are no inhibitors present in the extract of the mixture that inhibit PCR and also to serve as a means of estimating the amount of Aloe DNA present in the sample, using the amplification efficiency of the internal control. The use of 5' radioactively labeled primers could be used to quantitate the amount of amplified product after separation of fragments and primers. Standard curves could be used to relate the amount of PCR product to starting template concentrations and hence to the starting DNA concentration in the extract.

The following examples are provided for illustrative purposes only and are not intended to limit the scope of the invention.

EXAMPLES

Materials

The whole plant dry leaf extract used in the following examples was supplied by Aloecorp (Irving, Tex.), in lyophilized form. The dry leaf extract was prepared by "whole-leaf processing" of the leaves of the Aloe barbadensis plant. Briefly, whole leaves were ground and filtered to yield a green viscous gel, treated with cellulase and then treated with activated carbon at 80° C. for 30 minutes, and finally filtered through diatomaceous earth prior to lyophilization. PCR primers were purchased from Operon Technologies and used without further purification.

Example 1

Isolation of DNA From Aloe to Use as PCR Standard

CTAB Extraction From Fresh Aloe Tissue

DNA was isolated from the mature leaf tissue of Aloe barbadensis (A. barbadensis), Aloe capensis (A. capensis) and Aloe arborescins (A. arborescins) by modification of the cetyltrimethylammonium bromide (CTAB) procedure (Doyle and Doyle (1987) Phytochem. Bull. 19:11–15). Briefly, leaves were harvested, cut into 1 cm slices with a scalpel blade, frozen in liquid nitrogen and stored at −70° C. until use. Frozen tissue (2.5 g) was first ground with dry ice in a coffee grinder and then ground with dry ice crystals using a mortar and pestle. The frozen powder was quickly transferred to 15 mL of a detergent solution (3% CTAB (Sigma Chemical Company (St. Louis, Mo.)), 1.4 M NaCl, 20 mM EDTA, 100 mM Tris HCl (pH 8.0), 0.2% β-mercaptoethanol (BME) at 60° C. and incubated with occasional mixing for 35 minutes. An equal volume of $CHCl_3$:isoamyl alcohol (24:1) was added and the emulsion rocked gently for 10 minutes. Phases were separated by centrifugation at 4000 rpm in a Joun centrifuge for 30 minutes at 4° C. The aqueous supernatant was removed with a large bore pipet. Heat treated ribonuclease (650 μg) (Sigma R-5125 type IIIA) from bovine pancreas was added and the mixture was incubated at room temperature for 30 minutes. After 30 minutes, one volume of ice cold ethanol was added and the phases were mixed gently. DNA was spooled out and rinsed briefly in 70% ethanol, 10 mM $NH_4OAc$. The DNA was resuspended in 2 mL TE buffer (10 mM Tris HCl, 0.1 mM EDTA) and ethanol precipitated once from 0.3 M NaOAc (pH 5.2) and once from 3.75 M $NH_4OAc$ (pH 7.5).

Guanidine Thiocyanate Extraction From Whole Dry Leaf Extract.

Extraction 1

Dry leaf extract (1 g) was dissolved in 25 mM EDTA, 0.15 M NaOAc, 4.2 M guanidine thiocyanate (GnSCN) and 0.7% BME. The pH was adjusted to 5.0 with 1 M NaOH, an equal volume of 91% isopropanol was added and the mixture was centrifuged at 400 rpm, for 25 minutes at 4° C. in a Joun centrifuge. The pellet was resuspended in 7 mL of TE buffer and 3.5 mL 7.5 M $NH_4OAc$ pH 7.5 and precipitated overnight with one volume of isopropanol at −20° C. The precipitate was collected by centrifugation for 30 minutes at 4000 rpm. The pellet was reprecipitated from 12 mL of a solution of 1.8 M NaCl, 0.1 mM EDTA with 0.5 volume isopropanol and 0.5 volume ethanol for 3 hours at −20° C. and the precipitate was collected by centrifugation as described above. The pellet was reprecipitated from 2.8 mL TE buffer, 0.5 volumes $NH_4OAc$, and two volumes 70% isopropanol for 2 hours at −20° C. and collected in a microcentrifuge for 20 minutes at 12000×g. The final precipitation was from $NH_4OAc$ with the starting volume of TE reduced to 0.7 mL.

Extraction 2

Dry leaf extract (2 g) was dissolved in 5 mL GnSCN solution as described above, 15 mL of 1 M NaCl was added and the solution was precipitated with 1 volume of isopropanol (91%). The precipitate was resuspended and precipitated serially through four NH₄OAc/isopropanol precipitations with gradually decreasing volumes and increasing concentrations of isopropanol.

Extraction of DNA From Liquid Industrial Products

Solid GnSCN was added to the liquid to achieve a final concentration of 4.5 M. EDTA and buffer were added as described above for the dry leaf extract and samples were processed by serial precipitation as described above.

Example 2

Polymerase Chain Reactions

The polymerase chain reactions (PCR) were performed using the primers set forth in Table 1 and the DNA obtained using the extraction procedures set forth in Example 1. The rbcL primers were chosen using the PRIMER program from the *Aloe vera* rbcL sequence retrieved from the NCBI data base, and was used only as a control PCR before it was clearly established that the universal chloroplast primers and RAPD primers gave adequate amplification. The chloroplast tRNA gene primers were designed by Taberlet et al. (1991) Plant Molecular Biology 17:1105–1109. The $T_d$ of the oligonucleotides was calculated by nearest neighbor analysis using the program OLIGO (Rychlik and Rhoads (1989) Nucleic Acids Res. 17:8543–8551) and the $T_A$ estimated according to Rychlik et al. (1990) Nucleic Acids Res. 18:6409–6412. In some cases the $T_A$ had to be determined empirically. Random Amplified Polymorphic DNA (RAPD) primers OPAE(1–20) were used at $T_A$ 36° C. (Williams et al. (1993) Methods in Enzymol. 218:704–741).

TAQ polymerase was purchased from Promega Biotec and used according to the manufacturers instructions at 1.5 U/50 μL reaction. The concentration of magnesium was 1.5 mM in all reactions. The PCR reactions were carried out on an MJ Research thermocycler in 500 μL thin-walled, siliconized microfuge tubes (Biorad). Reactions (50 μL or 20 μL) were covered with one drop of molecular biology grade mineral oil from Sigma and nucleotides were purchased from Pharmacia. All of the PCR reactions began with a 3 minute incubation at 94° C. and ended with 3 minutes at 72° C. for a final extension. The denaturation cycle was 1 minute at 94° C. for all PCR reactions. $T_A$ (annealing temperature) was varied for the different primer pairs and was 1 minute for all PCR reactions. $T_E$ (extension temperature) was 72° C. in all cases and was 1 minute for the single PCR reactions and 2 minutes for the semi-nested PCR. The number of cycles was varied to help achieve the desired sensitivity.

The PCR products were detected using ethidium bromide staining (of electrophoretic bands after electrophoresis on 1.2% agarose (BioRad) gels in 0.04 M Tris acetate pH 7.8, 5 mM sodium acetate, 1 mM EDTA buffer containing (0.5 μg/mL ethidium bromide). Ethidium bromide intercalates and fluoresces under long wave UV light. Data is recorded by photography. More sensitive detection methods exist, such as use of radioactively labeled primers or hybridization to an internally amplified segment of DNA. The detection limit which can be achieved reproducibly with ethidium bromide staining of electrophoretic bands is 50 fg of total DNA in the PCR reactions reported here.

TABLE 1

PCR Primers.

| Primer | Marker | Sequence | SEQ ID NO: |
|---|---|---|---|
| rbcL-f | rbcL | AATGTATTTGGTTTCAAAGCCC | 1 |
| rbcL-r | rbcL | CTTTAATTTCACCTGTTTCGGC | 2 |
| A1 | trnL-trnF intergenic | ATTTGAACTGGTGACACGAG | 3 |
| B1 | trnL-trnF intergenic | GGTTCAAGTCCCTCTATCCC | 4 |
| A2 | trnT-trnL intergenic | TCTACCGATTTCGCCATATC | 5 |
| B2 | trnT-trnL intergenic | CATTACAAATGCGATGCTCT | 6 |
| A3 | trnL intron | GGGATAGAGGGACTTGAAC | 7 |
| B3 | trnL intron | CGAAATCGGTAGACGCTACG | 8 |
| OPAE-01 | RAPD | TGAGGGCCGT | 9 |
| OPAE-10 | RAPD | CTGAAGCGCA | 10 |
| OPAE-11 | RAPD | AAGACCGGGA | 11 |
| OPAE-19 | RAPD | GACAGTCCCT | 12 |

TABLE 2

DNA Content in Extracts of Aloe.

| Sample | DNA extracted |
|---|---|
| fresh *Aloe barbadensis* leaf tissue | 10 μg/g |
| *Aloe barbadensis* dry leaf extract freeze dried | 1.8 μg/g |
| Naturally ALOE drink | 1.0 pg/ml |
| Aloe gel 1:1 decolorized | <1.0 pg/ml |

TABLE 3

Aloe barbadensis B3A1 Region of Chloroplast Genome[1].

CGAAATCGGTAGACGCTACG

GACTTGATTGGATTGAGCCTTAGTATGGAAACCTGCTAAGTGGTAACTTCCAAATTCAGAGAATCCCTGGAAC

TAAAAATGGGCAATCCTGAGCCAAATCTTTTTTTTTTTTGAAAAACTGATGAATCGGACAAGAATAAAAAAAGATAG

GTGCAGAGACTCAATGGAAGCTGTTCTAACGAATGGAGTTGATTACGTTGCGTTGGTAGCAGGAATCCTTCTTTCGAA

ATTAAAGAAAGGATGACCTGTATATCTAAGACATACGTATACATACTGACATAGCAAACAATTAATCACAAACCG

AATCCATTACCATTATATATATATATGCAAAATTCAGAGTTATTGTGGATCTATTCCAATCGACGTTGAAGGAAG

AATCGAATATTCAGTGATCCTATCACTCATTCCAGAGTTTGATAGGCCTTTTTTTTTTGAAAAACT

GATGAATTGGACGAGAATAAAGAGAGAGTCCCATTCTACATGTCAATACCGACAACAATGAAATTTATAGTAAGAGG

TABLE 3-continued

*Aloe barbadensis B3A1 Region of Chloroplast Genome[1].*

*AAAATCCGTCGACTCTTAGAAATCGTGA*

GGTCAAGTCCCTCTATCCCC

AATAAAAAGCCCATTTTTCCCCATAAAAAGCCCATTTT

ACTTCTTAACTATACTATTTATCTTCTTTTTTTTTCATAAGTAGTT<u>CAAGTTCAAAGAAAA</u>

<u>TTCAA</u>TATCTTTCTCATTGATTCTACCCTTTCCCAAACAAATG<u>GGTCCGAATAGATTTTTG</u>

TCTTATCCCAATTTGGTTTGAATAGATACGATATCTGTGCATATGAATATATATGGGCAAG

GAATTTCCATTGTTGAATCATTCACAGCCCATATCAGTATTTTTCCATTTACAAATACAAAG

AAAGTCTTCTTTTTGAAGATCTAAGAAATTCATGGACTAGGTCAATTTTTTGAATACTTT

AATTTAAATATTTCAATGATTTTTTTTTTTAATAATTAATATTGAATTTCTTTATTTTTAGT

CTATTTAATTTACCAAGCACTCTACTAGGATGATGCGCGGGAAATGGTCGGGAT

AGCTCAGTTGGTAGAGCAGAGGACTGAAAAT

CCTCGTGTCACCAGTTCAAAT

(SEQ ID NO:13)

[1]Primers used for PCR and sequencing are in bold. Italics indicate sequences from *A. capensis* and *A. arborescens*. Two new primers in *trnL* intron and two new primers in *trnL-trnF* intergenic region are underlined. The inside pair should be unique to *A. barbadensis*.

TABLE 4

*Aloe barbadensis* Chloroplast *trnL* Gene (B3A3) Compared to *Aloe arborecens* and *Aloe capensis*[1].

```
PRIMERB3/  trnL /10 intron
================
GTAGACG/CTACGGA
==============GA

CTTGATTGGATTGAGCCTTAGTATGGAAACCTGCTAAGTGGTAACTTCCAAATTCAGAGAATCCCTGGAAC

CTTGATTGGATTGAGCCTTAGTATGGAAACCTGCTAAGTGGTAACTTCCAAATTCAGAGAATCCCTGGAAC

CTTGATTGGATTGAGCCTTAGTATGGAAACCTGCTAAGTGGTAACTTCCAAATTCAGAGAATCCCTGGAAC

TAAAAATGGGCAATCCTGAGCCAAATCTTTTTTTTTTTTGAAAAACTGATGAATCGGACAAGAATAAAAAAAGATAG
                                          T                             A   G
                       --                  T

GTGCAGAGACTCAATGGAAGCTGTTCTAACGAATGGAGTTGATTACGTTGCGTTGGTAGCAGGAATCCTTCTTTCGAA
    A                                                  C
            T             T

ATTAAAGAAAGGATGACCTGTATATCTAAGACATACGTATACATACTGACATAGCAAACAATTAATCACAAACCG
            A
            A                                                          G

AATCCATTACC--------ATTATATATATATATGCAAAATTCAGAGTTATTGTGGATCTATTCCAATCGACGTTGA
    A      TATATTATAT    - G             T                              T
    TA     TATATGATAT    T G

AGGAAGAATCGAATATTCAGTGATCCTATCACTCATTCCAGAGTTTGATAGGCC----TTTTTTTTTTGAAAAACT
                                                      -CTT
                                                      CTTT

GATGAATTGGACGAGAATAAAGAGAGAGTCCCATTCTACATGTCAATACCGACAACAATGAAATTTATAGTAAGAGG
    A
    A

================================   A. barbadensis (SEQ ID NO:14)
```

TABLE 4-continued

*Aloe barbadensis* Chloroplast *trnL* Gene (B3A3) Compared to *Aloe arborecens* and *Aloe capensis*[1].

```
AAAATCCGTCGACTCTTAGAAATCGTGA/GG    A. aborescens    (SEQ ID NO:15)
AAAATCCGTCGACTCTTAGAAATCGTGA/GG    A. capensis      (SEQ ID NO:16)

trnL                     / PRIMER A3
```

[1]A comparison of the sequences of *Aloe barbadensis*, *Aloe arborescens* and *Aloe capensis*. Substitutions, deletions and insertions in *A. arborescens* and *A. capensis* are notated below and the *A. barbadensis* sequence. The underlined sequence is the sequence that could be used for the forward primer for the aloe industrial assay. The sequence change in the underlined region is unique to *A. barbadensis*.

TABLE 5

*Aloe barbadensis trnL-trnF* Intergenic Region Compared to *Aloe arborescens* and *Aloe capensis*[1].

```
primer b1
====================TCCCCAATAAAAAGCCCATTTT
============TCCCTCTA
=======TCAAGTCCCTCTA ACTTCTTAACTATACTATTTATCTTCTTTTTTTT-CATAAGTAGTTCAAGTTCAAAGAAAA-
                                     T          ------         A
                                     T          ------         A TTCAATATCTTTCTCATTGATTCTACCCTTTCCCAAACAAATGGGTCCGAATAGATTTTTG
                                                            A
                                                            G TCTTATCCCAATTTGGTTTGAATAGATACGATATCTGTGCATATGAATATATATGGGCAAG
               A     A      C                                A
           G   A     A      T                                A

GAATTTCCATTGTTGAATCATTCACAGCCCATATCAGTATTTTTCCATTTACAAATACAAAG
A
G          A A

AAAGTCTtCTTTTTGAAGATCTAAGAAATTCATGGACTAGGTCAATTTTTTGAATACTTT
               A
               A    T

AATTTAAATATTTCAATGATTTTTTTTTTTAATAATTAATATtGAATTtCTTTATTTTTAGT
    C     A             ---  A---  -   -
    C     A             ----  -         -

CTATTTAATTTACCAAGCACTCTACTAGGATGATGCGCGGGAAATGG

CTATTTAATTTACCAAGCACTCTACTAGGATGATGCGCGGGAAATGG

CTATTTAATTTACCAAGCACTCTACTAGGATGATGCGCGGGAAATGG trnF                             / primer A1

TCGGGATAGCTCAGTTGGTAGAGCAGAGGACTGAAAATCCT=========== A. barbadensis  (SEQ ID NO:17)
                                        CGTGTCACC     A. aborescens   (SEQ ID NO:18)
                                        CGTGTCACCAGT  A. capensis     (SEQ ID NO:19)
```

[1]The portion of primers that were sequenced are shown in bold. Bold italics shows an insertion that may be used to distinguish *A. barbadensis* from other species and be the basis of the validation of an *A. barbadensis* PCR assay. The underlined region was the primer chosen. All primers were tested by PRIMER program to automatically check for adequate Td and possible primer annealing properties that would be undesirable. Primers spanning this region could be designed to amplify *A. capensis* and *A. arborescens* instead of *A. barbadensis*.

TABLE 6

OPAE-19 PCR Using Primers 4F and 4R[1].

```
CACtCCAAGgANAAATGGTCTTCTCTCTATGAGATACACTCACAACAgAAAGAgAAGTCAtCACTGCACTGAC        (SEQ ID NO:20)

AAAACATAATGGCtCCACCTGAAAGTTTGTATGGTGAAAAGAGCCCAAAAgAACaCCTCAATGGATGTNGCCAACC
```

TABLE 6-continued

OPAE-19 PCR Using Primers 4F and 4R[1].

TGGATATGAATAAAGCTCTGGAAAGAAGGAAACTCTGTGGTGTTTTCCAATGAACCACTCAtACCACAAATCCACA

ATCGATCACCAACCATATCTG

CTGAGTAcTGTCAGATATcATGCtTGTCTGCATAtTGTATGAAGGCATata     (SEQ ID NO:21)

AcATCcATGAGCtACGCTACCtTAGAAtCCGAGTACTACCgCgCCaTGAtATAGtCTtCACCgtcAC

[1]The OPAE 19-4F and 4R primers are shown in bold. These sequences were determined on one strand, thus bases in small caps indicate possible ambiguities. Data base searches suggest that SEQ ID NO:20 is not chloroplast and is unique to the Aloe species. SEQ ID NO:21 may be useful to find a third primer for nesting.

TABLE 7

OPAE-19 PCR Using Primers 7F and 7R[1].

CCTTGTGGTGtGGACtACATgTCAG GaTTCAGgTGTACtCCGGcaTCTgGTCtACTAACTCgCtTAGACCCCTTA     (SEQ ID NO:22)

CCTTtCTCACAGATGAATAGTtGAACCtCTANNCTAATtTTATAAgATGTaGCTCCATTTGTGAATTTCTAGACC

GGATCATAATTTATgTACGGGTaTCAAGTATCTtAATGCttTGTAGACATGCTCtCACCCATACGGAAAGGTCCC

TGActGGTCGgAAATTCGCGCTCCAtCACCCCgACCCCATGTaTAGGTtAGTaTTTCCTTCCGGATgCTTGTTAc

AGctCCGCgAGGTGACCGNaCGTCtTAgTAtaTTCCCTTGTGTTaTATTTCCCCTTGAGTAATaTAaGagaCtGA

TcAATTgaCGGCATAAtTATcATACTtGtAAAATTCTAATaTcTGCaTGTCTCaTGCCTAATTAgAATATGATGATa

AGTCCa tctGGaGtACCTATGGACCagtACCGAGAAAtgATTTCCtGAAAcAGATTTTGGaAa     (SEQ ID NO:23)

AGAACaatTAtAATTTAgCCGGGGaAgATTTTACtCATAtATTCCgAAAGAATTAGCCAtATCtaatATTAAtgATGA

TcATGCATGTTCtCaGAgagtCAtGtATATGGAGcCCGGgAccACCtCAAtCGAgaTAcCAGTagGTCCCAGAACAAA

[1]The OPAE 19-7F and 7R primers are shown in bold. These sequences were determined on one strand, thus bases in small caps indicate possible ambiguities.

TABLE 8

OPAE-19 PCR Using Primers 8F and 8R[1].

GAGAGATcCAGTCGATCACTAtAAATGTGGATCTTAgCCCAACTGTTCGgCATACTGGAGATCCTCCaTCGGTA     (SEQ ID NO:24)

GGATACgGATCCCCTGTCTCAAAATCATCCTCATACAAACCTCATGCACCatGgTCCTGGTGGTCAACTAaGCTgT

CAGaTAAAGTaGCCAAaTaACAGAATACAtCTAGATAATAACTGCAGAgAAATACTGATATGAACTAaCAGgTATGC

AATGGAAAATACTACAGTTGTTATCTTTCGTCCATTTTAtTAATggTTGGAgAGCATAATCTAACAATAaTGGCT

CAacGGATACCcaCAGGGTGGATATCTGTATCACAGgTACCGATATCTAGcTCAATGCATTGTCATCAACCTTCACA

TCgGCATGCCGTATCCCTTTCCCAaAC

[1]The OPAE 19-8F and 8R primers are shown in bold. The sequence was determined on one strand, thus bases in small caps indicate possible ambiguities.

TABLE 9

Aloe Specific PCR Primers.

| Aloe Specific Primers | Name | Amplified Fragment Size (bp) | SEQ ID NO: |
|---|---|---|---|
| CAAACCGAATCCATTACC | av-f | 378 | 25 |
| TTGAATTTTCTTTGAACTTG | av-r |  | 26 |
| GATAGGTGCAGAGACTCAATG | aloe-f | 587 | 27 |
| AGACAAAAATCTATTCGGA | aloe-r |  | 28 |
| CTGCACTGACAAAACATAATG | opae19-4f | 169 | 29 |

TABLE 9-continued

Aloe Specific PCR Primers.

| Aloe Specific Primers | Name | Amplified Fragment Size (bp) | SEQ ID NO: |
|---|---|---|---|
| GATCGATTGTGGATTTGTG | opae19-4r | | 30 |
| CCTGTCTCAAAAATCATCCTC | opae19-8f | 293 | 31 |
| TGTGAAGGTTGATGACAATG | opae19-8r | | 32 |

I claim:

1. A method for identifying Aloe using the Polymerase Chain Reaction (PCR) comprising the steps of:
   a) extracting DNA from a sample containing Aloe;
   b) amplifying the DNA using PCR, wherein said PCR is performed using PCR primers selected from the group set forth in Table 1 (SEQ ID NOS:3–12);
   c) sequencing the amplified DNA; and
   d) comparing the sequence of the amplified DNA obtained from PCR with the sequence of DNA obtained from a known sample of Aloe.

2. The method of claim 1 wherein the Aloe is selected from the group consisting of *Aloe barbadensis, Aloe capensis* and *Aloe arborescins*.

3. The method of claim 1 wherein said PCR is performed using a semi-nested technique.

4. A nucleotide sequence selected from the group consisting of SEQ ID NOS:13–32 or a fragment thereof.

5. A method for differentiating between different species of Aloe comprising the steps of:
   a) extracting DNA from an unknown sample containing Aloe;
   b) amplifying the DNA by PCR using primers specific for a particular species of Aloe; and
   c) comparing the amplified DNA from the unknown sample obtained in step (b) with PCR products obtained from known species of Aloe.

6. A method for determining the amount of Aloe DNA present in a sample comprising the steps of:
   a) extracting DNA from an unknown sample containing an internal control;
   b) amplifying the DNA by PCR using primers specific for Aloe; and
   c) measuring the amount of amplified DNA.

7. A method for identifying Aloe using the Polymerase Chain Reaction (PCR) comprising the steps of:
   a) extracting DNA from a sample containing Aloe;
   b) amplifying the DNA using PCR, wherein said PCR is performed using primers specific for Aloe;
   c) sequencing the amplified DNA; and
   d) comparing the sequence of the amplified DNA obtained from PCR with the sequence of DNA obtained from a known sample of Aloe.

8. The method of claim 7 wherein said PCR is performed using primers specific for Aloe selected from the group set forth in Table 9 (SEQ ID NOS:25–32).

* * * * *